United States Patent [19]

Steinmann

[11] Patent Number: 5,710,240
[45] Date of Patent: Jan. 20, 1998

[54] CONDENSATES OF BUTYNE-LINKED HINDERED AMINES

[75] Inventor: Alfred Steinmann, Praroman, Switzerland

[73] Assignee: Ciba Specialty Chemicals Corporation, Tarrytown, N.Y.

[21] Appl. No.: 606,897

[22] Filed: Feb. 26, 1996

[30] Foreign Application Priority Data

Mar. 2, 1995 [CH] Switzerland .................. 596/95

[51] Int. Cl.$^6$ .................. C08G 69/44; C08G 73/16
[52] U.S. Cl. .................. 528/289; 528/27; 528/73; 528/68; 528/269; 528/270; 528/392; 546/186; 546/187; 546/188; 546/190; 546/191
[58] Field of Search .................. 546/186, 187, 546/188, 190, 191; 528/27, 73, 68, 269, 270, 289, 392

[56] References Cited

U.S. PATENT DOCUMENTS

| | | | |
|---|---|---|---|
| 3,085,093 | 4/1963 | Meltzer et al. | 546/186 |
| 3,755,586 | 8/1973 | Sanzari et al. | 514/316 |
| 3,940,363 | 2/1976 | Murayama et al. | 524/102 |

FOREIGN PATENT DOCUMENTS 0685465  12/1995  European Pat. Off. .

OTHER PUBLICATIONS

J. Org. Chem. vol. 27, pp. 1695–1703 (1962).
Journal of Medicinal Chemistry, 1970, vol. 13, No. 4, pp. 651–657.
Organic Magnetic Resonance, vol. 15, No. 3, (1981) pp.285–287.
Organic Magnetic Resonance, vol. 19, No. 2 (1982) pp. 91–94.
Eur. J. Med. Chem. (1992), vol. 27, pp. 93–99.
Derw. Abst. 96–012315 of EP 685,465 (1995).

Primary Examiner—C. Warren Ivy
Assistant Examiner—Garth Dahlen
Attorney, Agent, or Firm—David R. Crichton; Victoria M. Malia

[57] ABSTRACT

The invention relates to compounds of the formula I

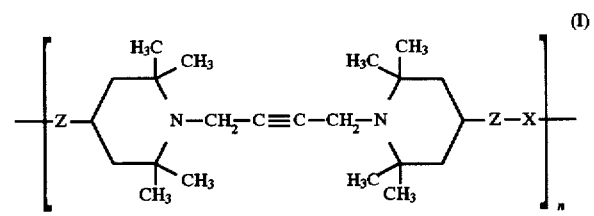
(I)

in which n is a number in the range from 1 to 100;

X is $-R^7-$, $-CO-$, $-CO-CO-$, $-CO-R^2-CO-$, $-CO-NH-R^5-NH-CO-$, $-CO-O-R^6-O-CO-$ or

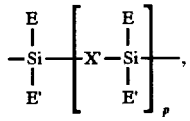

where p is a number in the range from 0 to 6, X' is O or a direct bond, E is $C_1-C_{12}$alkyl, phenyl, $C_7-C_{12}$phenylalkyl or $C_5-C_{12}$cycloalkyl, and E' is hydrogen or is as defined for E;

Z, when X is $R^7$, is O or $NR^1$; Z, when X is

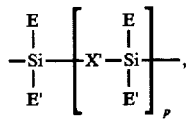

is O; and

Z, in all other cases, is O, NH or $NR^1$;

$R^1$ is $C_1-C_4$alkyl, $C_7-C_9$phenylalkyl, $C_5-C_7$cycloalkyl, $C_2-C_8$alkanoyl, benzoyl or $C_1-C_4$alkyl-substituted benzoyl;

$R^2$ and $R^7$ are $C_1-C_{18}$alkylene; $C_2-C_{18}$alkylene which is interrupted by O or S; phenylene; a mixed aromatic/aliphatic radical containing 7 to 12 carbon atoms; naphthylene; or an $-R^4-D-R^4-$ radical;

$R^4$ is 1,4-cyclohexylene or 1,4-phenylene; and $R^6$ is phenylene, naphthylene or

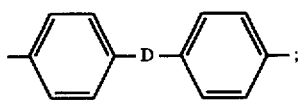

$R^5$, when Z is O, is as defined for $R^6$; and $R^5$, when Z is NH or $NR^1$, is as defined for $R^6$; and D is $C_1-C_3$alkylene, $-S-$, $-SO-$, $-SO_2-$, $-CO-$, $-O-$, $-NH-$ or $-NR^1-$.

Compounds of the formula I can advantageously be used for stabilizing organic material against the harmful effects of light, oxygen and/or heat.

10 Claims, No Drawings

CONDENSATES OF BUTYNE-LINKED HINDERED AMINES

The invention relates to novel oligomeric or polymeric compounds which can be obtained by condensation of 1,4-bis(4-hydroxy-2,2,6,6-tetramethylpiperidin-1-yl)but-2-yne or corresponding diamines with suitable reaction partners, to the use thereof for stabilizing organic material against oxidative, thermal or actinic degradation, to corresponding stabilized compositions, and to a stabilization process.

A number of scientific publications describe 1-butynyl-2,2,6,6-tetramethylpiperidines whose piperidinyl ring is unsubstituted in the 4-position, and their possible use as medicaments; for example M. E. Zuhair et al., *Eur. J. Med. Chem.* 27, 93 (1992) (C.A. 117:26405v); J. M. A. Al-Rawi et al. in *Org. Magn. Reson.* 19, 91 (1982) (C.A. 97:155132w) and *Org. Magn. Reson.* 15, 285 (1981) (C.A. 95:60789k); B. Karlen et al., *J. Med. Chem.* 13, 651 (1970) (C.A. 73:44857w).

1,6-Bis(2,2,6,6-tetramethylpiperidin-1-yl)hexadiyne, whose piperidinyl rings are unsubstituted in the 4-position, is described in the publications U.S. Pat. No. 3,755,586 (C.A. 80:19550c); W. B. Lutz et al., *J. Org. Chem.* 27, 1695 (1962); and U.S. Pat. No. 3,085,093 (C.A. 59:9998e) as a pharmaceutically active compound.

It has now been found that certain derivatives of butyne-linked hindered mines can be converted into chain-like molecules which, surprisingly, are highly suitable for use as stabilizers for organic material.

The invention therefore relates firstly to novel compounds of the formula I

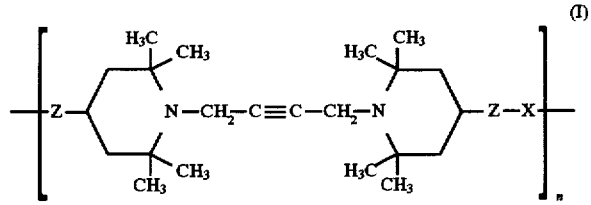
(I)

in which n is a number in the range from 1 to 100;

X is —$R^7$—, —CO—, —CO—CO—, —CO—$R^2$—CO—, —CO—NH—$R^5$—NH—CO—, —CO—O—$R^6$—O—CO— or

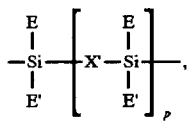

, where p is a number in the range from 0 to 6, X' is O or a direct bond, E is $C_1$–$C_{12}$alkyl, phenyl, $C_7$–$C_{12}$phenylalkyl or $C_5$–$C_{12}$cycloalkyl, and E' is hydrogen or is as defined for E;

Z, when X is $R^7$, is O or $NR^1$; Z, when X is

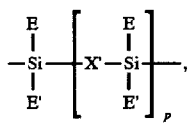

is O; and

Z, in all other cases, is O, NH or $NR^1$;

$R^1$ is $C_1$–$C_8$alkyl, $C_7$–$C_9$phenylalkyl, $C_5$–$C_7$cycloalkyl, $C_2$–$C_8$alkanoyl, benzoyl or $C_1$–$C_4$alkyl-substituted benzoyl;

$R^2$ and $R^7$ are $C_1$–$C_{18}$alkylene; $C_2$–$C_{18}$alkylene which is interrupted by O or S; phenylene; a mixed aromatic/aliphatic radical containing 7 to 12 carbon atoms; naphthylene; or an —$R^4$—D—$R^4$— radical;

$R^4$ is 1,4-cyclohexylene or 1,4-phenylene; and $R^6$ is phenylene, naphthylene or

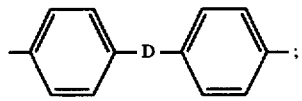

$R^5$, when Z is O, is as defined for $R^2$; and
$R^5$, when Z is NH or $NR^1$, is as defined for $R^6$; and
D is $C_1$–$C_3$alkylene, —S—, —SO—, —$SO_2$, —CO—, —O—, —NH— or —$NR^1$—.

The saturation of the chain ends in the formula I arises from the preparation conditions, which are described below. In general, the compounds of the formula I have the terminal group A at the Z terminal and the terminal group B at the X terminal and thus conform to the formula Ia

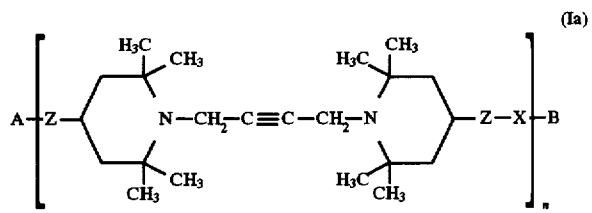
(Ia)

where n, X and Z are as defined above;

A is hydrogen or a terminal group of the formula —X—Z';

B is a terminal group of the formula

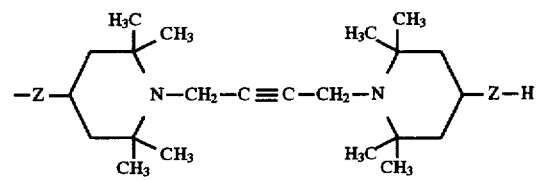

or —Z'; and

Z' is OH, $NH_2$ or $OR^1$.

Alkylene here generally denotes a polyvalent, in particular a bivalent, saturated aliphatic hydrocarbon radical, in which the two bonds can be localized on the same or different carbon atoms.

$C_1$–$C_8$alkyl $R^1$ is methyl, ethyl, propyl, butyl, pentyl, hexyl, heptyl or octyl; $C_7$–$C_9$phenylalkyl $R^1$ is, for example, benzyl, 1-phenylethyl or 2-phenylethyl; and $C_5$–$C_7$cycloalkyl $R^1$ is cyclopentyl, cyclohexyl or cycloheptyl.

$R^1$ as the radical of an organic carboxylic acid is, for example, acetyl, benzoyl, propanoyl, butanoyl, pentanoyl, hexanoyl, heptanoyl or octanoyl, preferably acetyl or benzoyl, in particular acetyl.

$C_1$–$C_{18}$alkylene $R^2$ and $R^7$ are methylene, ethylene, propylene, butylene, pentylene, hexylene, heptylene, octylene, nonylene, decylene, undecylene, dodecylene, tridecylene, tetradecylene, pentadecylene, hexadecylene, heptadecylene or octadecylene. Straight-chain alkylene is preferred. $C_1$–$C_{12}$alkylene is likewise preferred. Straight-chain $C_2$–$C_{12}$alkylene is particularly preferred.

$R^2$ and $R^7$ as $C_2$–$C_{18}$alkylene which is interrupted by O or S are, for example, $(CH_2)_m$—S—$(CH_2)_j$ or $(CH_2)_m$—O—$(CH_2)_j$, where the sum of the integers m+j is a number in the range from 2 to 18; examples are —$CH_2$—S—$CH_2$— and —$CH_2$—O—$CH_2$—.

$R^2$ and $R^7$ as a mixed aromatic/aliphatic radical containing 7 to 12 carbon atoms are divalent hydrocarbon radicals containing at least one saturated aliphatic unit and an aryl unit, where the bonds are localized either both on the aryl unit or both on an aliphatic unit or one on any aryl unit and one on an aliphatic unit. Aryl units are taken to mean essentially phenyl, phenylene, naphthyl or naphthylene. The radicals mentioned therefore include those of the formulae

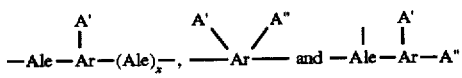

where Ar is in each case an aryl unit as defined above, Ale is $C_1$–$C_6$alkylene, A' and A", independently of one another, are H or $C_1$–$C_6$alkyl, and the index x is 0 or 1, with the proviso that the total number of carbon atoms is 7 to 12.

Preferred such radicals include

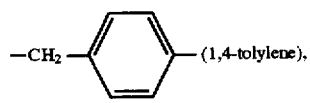

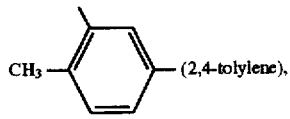

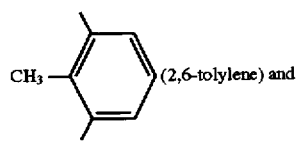

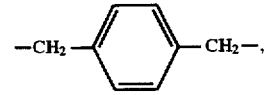

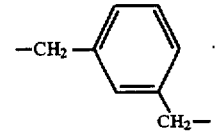

E is particularly preferably phenyl or methyl, and E' is particularly preferably H, phenyl or methyl.

Z is preferably O or NH, in particular O.

X is preferably —CO—, —CO—CO—, —CO—$R^2$—CO—, —CO—NH—$R^5$—NH—CO— or

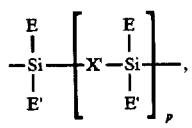

in particular —CO—, —CO—CO— or —CO—$R^2$—CO—.

p is preferably 0 or 1.

$R^2$ is preferably phenylene, $CH_2$—S—$CH_2$, $CH_2$—O—$CH_2$,

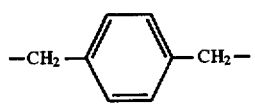

or $C_1$–$C_{12}$alkylene, in particular straight-chain $C_1$–$C_{12}$alkylene.

When Z is O, $R^5$ is preferably $C_3$–$C_{12}$alkylene, phenylene, naphthylene, cyclohexylene, tolylene, ethylene which is interrupted by phenylene, or —$R^4$—$CH_2$—$R^4$—, particularly preferably straight-chain $C_4$–$C_8$alkylene, phenylene,

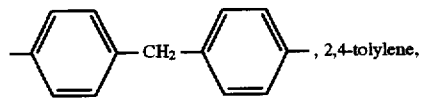, 2,4-tolylene, 2,6-tolylene, 1,5-naphthylene, 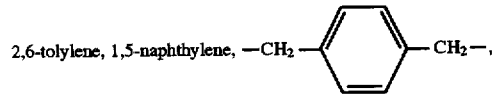

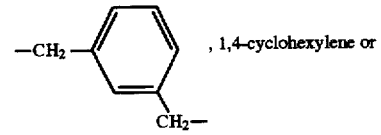, 1,4-cyclohexylene or

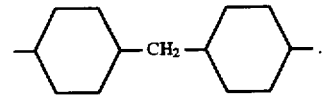.

$R^5$ and $R^6$ are preferably phenylene.

$R^7$ is preferably alkylene, in particular $C_1$–$C_{12}$alkylene.

D is preferably —O—, —CO—, —NH— or —$NR^1$—, in particular —CO—; the meaning —$CH_2$— is also of particular industrial interest.

The compounds of the formula I can be, for example, oligomeric or polymeric compounds. They are frequently mixtures of compounds having different degrees of polymerization. The invention preferably relates to compounds of the formula I in which n is an integer in the range from 4 to 80, in particular in the range from 5 to 50, especially from 10 to 30.

Preference is likewise given to compounds of the formula I in which X is —CO—, —CO—CO—, —CO—$R^2$—CO—,

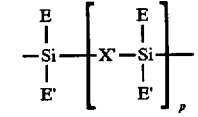

or —CO—NH—$R^5$—NH—CO—, where p is 0 or 1, X' is O or a direct bond, E' is hydrogen, phenyl or methyl, and E is phenyl or methyl;

$R^1$ is $C_1$–$C_8$alkyl, benzyl, $C_2$–$C_8$alkanoyl, benzoyl or cyclohexyl;

$R^2$ and $R^7$ are $C_1$–$C_{18}$alkylene; $C_2$–$C_{18}$alkylene which is interrupted by O or S; phenylene; a mixed aromatic/aliphatic radical containing 7 to 12 carbon atoms; naphthylene; or an —$R^4$—D—$R^4$— radical;

$R^4$ is 1,4-cyclohexylene or 1,4-phenylene;

$R^5$, when Z is O, is $C_3$–$C_{12}$alkylene, phenylene, naphthylene, cyclohexylene, tolylene, ethylene which is interrupted by phenylene, or —$R^4$—$CH_2$—$R^4$—; and D is $C_1$–$C_3$alkylene, —NH—, —NR$^1$, —CO— or —S—.

Particular preference is given to compounds of the formula I in which Z is O or NR$^1$;

X is —CO—CO—, —CO—R$^2$—CO—,

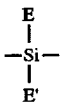

or —CO—NH—R$^5$—NH—CO—;

R$^2$ and R$^7$ are $C_1$–$C_{18}$alkylene; phenylene, CH$_2$—S—CH$_2$, CH$_2$—O—CH$_2$ or

and

R$^5$, when Z is O, is $C_3$–$C_{12}$alkylene, phenylene, naphthylene, cyclohexylene, tolylene, ethylene which is interrupted by phenylene, or —R$^4$—CH$_2$—R$^4$, where R$^4$ is as defined above; and R$^5$, when Z is NR$^1$ is phenylene;

especial preference is given to those in which n is an integer in the range from 5 to 50;

Z is an oxygen atom;

R$^2$ and R$^7$ are $C_1$–$C_{12}$alkylene or phenylene; and

R$^5$ is $C_3$–$C_{12}$alkylene, phenylene, naphthylene or cyclohexylene.

Compounds of the formula I belong, for example, to the following classes of compounds:

1. Polyesters when Z is O and X is —CO—R$^2$—CO—;
2. Polyurethanes when Z is O and X is —CO—NH—R$^5$—NH—CO—, or when Z is NH or NR$^1$ and X is —CO—O—R$^6$—O—CO—;
3. Polyamides when Z is NH or NR$^1$ and X is —CO—R$^2$—CO—;
4. Polyethers when Z is O and X is —R$^7$—;
5. Polycarbonates when Z is O and X is —CO— or —CO—O—R$^6$—O—CO—;
6. Polyamines, when Z is NR$^1$ and X is —R$^7$—;
7. Polyureas when Z is NH or NR$^1$ and X is —CO—NH—R$^5$—NH—CO— or —CO—;
8. Polysilanes or polysiloxanes, when X is

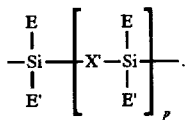

Preference is given to polyesters, polyethers and polyurethanes.

Compounds of the formula I in which Z is O are frequently prepared from a diol of the formula II:

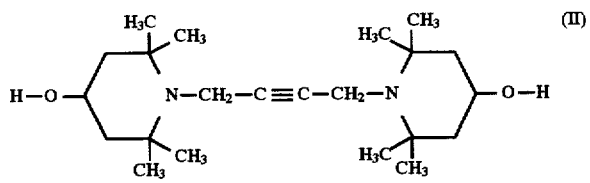

The compounds of the formula II can be obtained analogously to known preparation processes, as described, for example, in U.S. Pat. No. 3,085,093; *J. Org. Chem.* 27, 1695 (1962); *Eur. J. Med. Chem.* 27, 93 (1992); U.S. Pat. No. 4,386,127; and *J. Med. Chem.* 13, 651 (1970), and in the references cited therein. For example, 2,2,6,6-tetramethyl-4-hydroxypiperidine can be reacted with butynyl halides or dihalides or first with propargyl halide. The halides employed are frequently the chlorides, in particular the bromides. The resultant 1-propargyl-2,2,6,6-tetramethyl-4-hydroxypiperidine can be reacted with formaldehyde and further 2,2,6,6-tetramethyl-4-hydroxypiperidine to give the disubstituted butyne.

The compound of the formula II is preferably prepared by reacting an ester of an aromatic sulfonic acid of the formula III

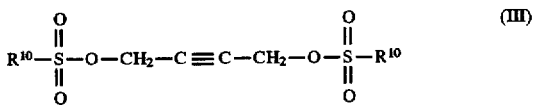

in which R$^{10}$ is phenyl or $C_1$–$C_8$alkyl—, $C_1$–$C_8$alkoxy— or halogen-substituted phenyl, with a compound of the formula IV

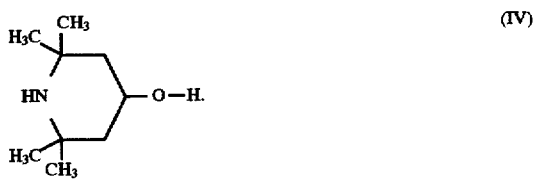

R$^{10}$ is preferably phenyl, tolyl, chlorophenyl or methoxyphenyl, in particular phenyl or tolyl. The starting material of the formula III used in this process is particularly preferably 2-butyne-1,4-diol ditosylate.

It is expedient to use about 2 equivalents of the compound of the formula IV per equivalent of the compound of the formula III. The compound of the formula IV can also advantageously be used in excess, for example in an amount of 1.5–4, in particular 2–3, equivalents of the compound of the formula IV per sulfonyloxy group in the compound of the formula III; the unreacted starting material can in this case be separated off from the product and reused in the reaction.

The reaction is expediently carried out in an inert solvent. Frequently used inert solvents are polar organic solvents, for example halogenated hydrocarbons, esters, ethers, ketones, amides, nitriles, tertiary amines or sulfoxides; examples of suitable solvents are dimethylformamide, tetrahydrofuran, dioxane, chloroform, triethylamine, pyridine, dibutyl ether, dimethyl sulfoxide and, particularly preferably, acetonitrile.

The temperature during the reaction can be in the range from 0° to 200° C., expediently from 20° to 160° C., particularly from 40° to 140° C.

The temperature of the reaction mixture can be kept in the boiling range (reflux) for the duration of the reaction. To this end, a reaction mixture containing solvents is warmed to the boiling point, generally under atmospheric pressure, and the evaporated solvent is condensed with the aid of a suitable condenser and fed back to the reaction mixture.

The reaction can be carried out in the absence of oxygen, for example by flushing with an inert gas, such as argon; however, oxygen does not always interfere, so that it may be possible to carry out the reaction without said measure.

When the reaction is complete, work-up can be carried out by customary methods; the mixture is expediently first diluted with water, for example by adding from 1 to 4 times the volume of ice-water to the reaction mixture; the product can subsequently be separated off directly or extracted, for example the ethyl acetate or chloroform. If extracted, the product can be isolated in a conventional manner by removing the solvent; this is expediently carried out after the organic phase has been dried. It is also possible to use further purification steps, for example washing with aqueous NaCl solution, dispersion of activated charcoal, filtering, recrystallization and/or distillation.

However, it is also possible to use the resultant compound of the formula II as a crude product without further purification in the subsequent condensation or addition reaction for the preparation of the compound of the formula I.

Some compounds of the formula III are known; they can be prepared, for example, as described in *Angew. Chem.* 104, 1652–1654 (1992) or analogously to the process described therein. Compounds of the formula IV are known, and some are commercially available.

The condensation or addition of compounds of the formula II to produce those of the formula I can be carried out in a manner known per se by reaction with corresponding bifunctional reaction partners. Examples of important reaction partners are dicarboxylic acids or dichlorides, anhydrides or diesters of dicarboxylic acids; diisocyanates; bischloroformates of the Cl—CO—O—$R^6$—O—CO—Cl type; dihalogen compounds; phosgene; lower alkyl carbonic acid diesters; dichlorosilanes or dichlorosiloxanes. The invention therefore also relates to compounds which can be obtained by polycondensation or polyaddition of compounds of the formula II with said bifunctional reaction partners.

Compounds of the formula I in which Z is NH or $NR^1$ are frequently prepared from amines of the formula VI

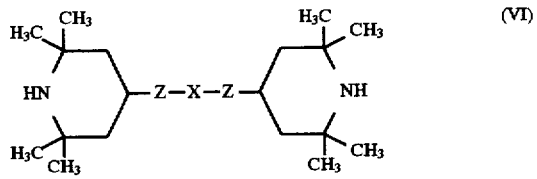

in which Z is NH or $NR^1$, and X and $R^1$ are as defined above.

Compounds of the formula VI can be obtained by known preparation processes or analogously to those as described, for example, in EP-A-388 535; *J. Org. Chem.* 37, 2015–18 (1992); JP-A-61-241 335 and JP-B-47-007 380.

The condensation or addition of compounds of the formula VI with or to those of the formula I can be achieved by reaction with an ester of an aromatic sulfonic acid of the formula III:

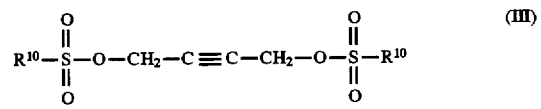

In this formula, $R^{10}$ is as defined above. The reaction conditions expediently correspond to the reaction conditions described above for the preparation of the compound of the formula II. Approximately equimolar amounts of the two starting materials of the formulae VI and III are usually used.

In detail, the following classes of compounds of the formula I can be obtained, for example:

1. Polyesters by reacting a diol of the formula II in which Z is O with a dicarboxylic acid, a dichloride or a diester of the dicarboxylic acid of the formula E—CO—$R^2$—CO—E, in which E is hydrogen, Cl or lower alkoxy, eg. $C_1$–$C_4$alkoxy, or a corresponding anhydride of a dicarboxylic acid. The reaction can be carried out, for example, analogously to one of the reactions as described in Methoden der Organischen Chemie [Methods of Organic Chemistry] (Houben-Weyl), Volume E20, Makromolekulare Stoffe [Macromolecular Substances], Thieme Verlag, Stuttgart 1987, pages 1405 et seq., in particular pages 1409 and 1411–1413.

2. Polyurethanes, for example, by reacting a diol of the formula II in which Z is O with a diisocyanate of the formula OCN—$R^5$—NCO analogously to one of the processes described in the abovementioned publication Methoden der Orgardschen Chemic (Houben-Weyl), Volume E20, pages 1587–1703. Polyurethanes are furthermore obtainable by reacting a diamine of the formula II in which Z is NH or $NR^1$, in particular NH, with a bischloroformate of the Cl—CO—O—$R^6$—O—CO—Cl type, in a corresponding manner to Methoden der Organisthen Chemie (Houben-Weyl), Volume E20, pages 1710–1715.

3. Polyamides by reacting firstly about 2 equivalents of the compound of the formula IV

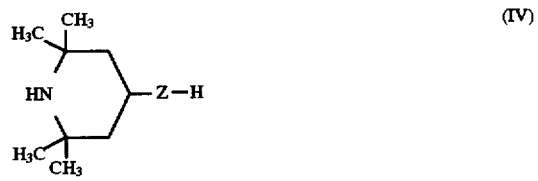

in which Z is NH or $NR^1$, with one equivalent of a dicarboxylic acid, a dichloride or a diester of a dicarboxylic acid of the formula E—CO—$R^2$—CO—E or E—CO—CO—E, in which E is hydrogen, Cl or lower alkoxy, or a corresponding anhydride of a dicarboxylic acid, if desired by one of the methods described in U.S. Pat. No. 3,684,765. The resultant intermediate of the formula

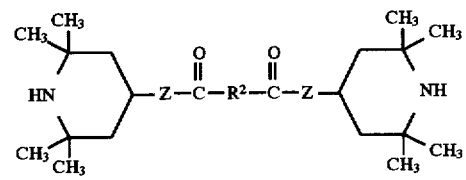

is subsequently expediently polycondensed with one equivalent of the above-described compound of the formula III

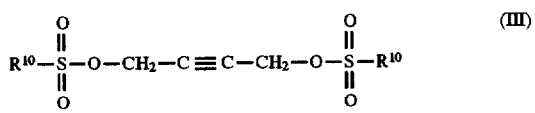

to give the compound of the formula I; the reaction conditions correspond essentially to the conditions described above for the reaction of the compounds of formula III and IV to give the compound of the formula II.

4. Polyethers by reacting a diol of the formula II or the corresponding dialkoxides with a dihalogen compound, for example a dichloride Cl—$R^7$—Cl, analogously to processes as described, for example, in Methoden der Organischen Chemic [Methods of Organic Chemistry] (Houben-Weyl), 4th edition, Volume XIV/2, Makromolekulare Stoffe [Macromolecular Substances], Part 2, Thieme Verlag, Stuttgart 1963, pages 582–583.

5. Polycarbonates by reacting a diol of the formula II in which Z is O with phosgene, bischloroformates of the Cl—CO—O—$R^6$—O—CO—Cl type, carbonic acid diesters or urea. The reaction can be carried out, for example, analogously to one of the reactions described in Methoden der Organischen Chemic [Methods of Organic Chemistry], (Houben Weyl), Volume E20, Makromolekulare Stoffe [Macromolecular Substances], Thieme Verlag, Stuttgart, 1987, pages 1446–1449.

6. Polyamines by reacting an amine of the formula VI in which Z is $NR^1$ and X is $R^7$ with a compound of the formula III

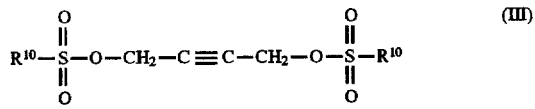

7. Polyureas by reacting an amine of the formula VI in which Z is NH or $NR^1$ and X is —CO— or —CO—NH—$R^5$—NH—CO— with a compound of the formula III.

8. Polysilanes or polysiloxanes by reacting a diol of the formula II or the corresponding dialkoxide with a compound of the formula

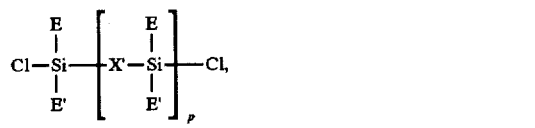

, in which E, E', X' and p are as defined above.

The novel compounds can advantageously be employed for stabilizing organic material against the harmful effects of light, oxygen and/or heat. They are distinguished by high substrate compatibility and good persistence in the substrate.

Examples of materials to be stabilized in accordance with the invention are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidenenorbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_{5-C9}$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

The invention therefore also relates to compositions comprising

A) an organic material which is sensitive to oxidative, thermal and/or actinic degradation and B) at least one compound of the formula I, and to the use of compounds of the formula I for stabilizing organic material against oxidative, thermal and/or actinic degradation.

The invention also relates to a process for stabilizing organic material against thermal, oxidative and/or actinic degradation in which at least one compound of the formula I is added to this material.

Of particular interest is the use of compounds of the formula I as stabilizers in synthetic organic polymers and corresponding compositions.

The organic materials to be protected are preferably natural, semi-synthetic or preferably synthetic organic materials. Particular preference is given to synthetic organic polymers or mixtures of such polymers, in particular thermoplastic polymers, such as polyolefins, especially polyethylene and polypropylene (PP), and coating compositions.

Binders (component A) for the novel coating compositions are principally all industrially conventional binders, for example those described in Ullmann's Encyclopedia of Industrial Chemistry, 5th Edn., Vol. A18, pp. 368–426, VCH, Weinheim 1991. These are generally film-forming binders based on a thermoplastic or thermosetting resin, mainly on a thermosetting resin. Examples thereof are alkyd, acrylic, polyester, phenolic, melamin, epoxy and polyurethane resins, and mixtures thereof.

The organic material to be stabilized can also be a photographic material; this is taken to mean, in particular, the materials described in Research Disclosure 1990, 31429 (pages 474–480) for photographic reproduction and other reproduction techniques.

In general, the compounds of the formula I are added to the material to be stabilized in amounts of from 0.01 to 10%, preferably from 0.01 to 5%, in particular from 0.01 to 2%, (based on the material to be stabilized). The novel compounds are particularly preferably used in amounts of from 0.05 to 1.5%, particularly from 0.1 to 0.5%.

The incorporation into the materials can be carried out, for example, by mixing or applying the compounds of the formula I and, if desired, further additives by industrially conventional methods. If they are polymers, in particular synthetic polymers, incorporation can take place before or during shaping, or by applying the dissolved or dispersed compound to the polymer, if necessary with subsequent evaporation of the solvent. In the case of elastomers, these can also be stabilized as latices. Another way of incorporating the compounds of the formula I into polymers comprises addition thereof before, during or directly after polymerization of the corresponding monomers or before crosslinking. The compound of the formula I can be added as such, but also in encapsulated form (for example in waxes, oils or polymers). In the case of addition before or during polymerization, the compounds of the formula I can also act as regulators for the chain length of the polymers (chain terminators).

The compounds of the formula I can also be added to the plastics to be stabilized in the form of a masterbatch, which comprises this compound in, for example, a concentration of from 2.5 to 25% by weight.

The incorporation of the compounds of the formula I can expediently be carried out by the following methods:

- as an emulsion or dispersion (for example to latices or emulsion polymers),
- as a dry mix during mixing of additional components or polymer mixtures,
- by direct introduction into the processing equipment (for example extruder, internal mixer, etc.),
- as a solution or melt.

The novel polymer compositions can be used in various forms or converted into various products, for example as (into) films, fibres, tapes, moulding compositions, profiles or as binders for paints, adhesives or putties.

In addition to the compounds of the formula I, the novel compositions can also comprise, as an additional component C, one or more conventional additives, as mentioned below, by way of example.

In addition to components A and B, the novel coating composition preferably comprises, as component C, a further light stabilizer of the sterically hindered amine, 2-(2-hydroxyphenyl)-1,3,5-triazine and/or 2-hydroxyphenyl-2H-benzotriazole type, for example as mentioned in the following list under points 2.1, 2.6 and 2.8.

The conventional additives are expediently employed in amounts of from 0.1 to 10% by weight, for example from 0.2 to 5% by weight, based on the polymer to be stabilized.

1. Antioxidants 1.1. Alkylated monophenols, for example 2,6-di-tert -butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl -4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methyl-undec-1'-yl) phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-do-decyl thiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-di-phenyl-4-octadecyloxyphenol, 2,6-di-tert -butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl) disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α-methylcyclohexyl) phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert -butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert -butylphenol), 4,4'-methylenebis(6-tert -butyl-2-methylphenol), 1,1-bis(5-tert-butyl-4-hydroxy-2-methylphenyl)butane, 2,6-bis(3-tert-butyl -5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl- 4-hydroxy2-methylphenyl) pentane.

1.7. O-, N- and S-benzyl compounds, for example 3,5,3', 5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl) dithioterephthalate, bis(3,5-di-tert-butyl-4-hydroxybenzyl)sulfide, isooctyl-3,5di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis-[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3, 5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3, 5-di-tert-butyl-4-hydroxybenzyl)phenol.

1.10. Triazine Compounds, for example 2,4-bis (octylmercapto)-6-(3,5-di-tert-butyl-4-hydroxyanilino)-1, 3,5-triazine, 2-octylmercapto-4,6-bis(3,5-di-tert-butyl-4-hydroxyanilino)-1,3,5-triazine, 2-octylmercapto-4,6-bis (3,5-di-tert-butyl -4-hydroxyphenoxy)-1,3,5-triazine, 2,4, 6-tris(3,5-di-tert-butyl-4-hydroxyphenoxy)-1,2,3-triazine, 1,3,5-tris-(3,5-di-tert-butyl-4-hydroxybenzyl) isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl) -hexahydro-1,3,5-triazine, 1,3,5-tris(3,5 -dicyclohexyl-4-hydroxybenzyl) isocyanurate.

1.11. Benzylphosphonates, for example dimethyl-2,5-di-tert-butyl-4-hydroxybenzylphosphonate, diethyl-3,5-ditert -butyl-4-hydroxybenzylphosphonate, dioctadecyl3,5-di-tert -butyl-4-hydroxybenzylphosphonate, dioctadecyl-5-tert-butyl -4-hydroxy3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]-octane.

1.14. Esters of β-(5-tert-butyl-4-hydroxy -3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo-[2.2.2] octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.17. Amides of β-(3,5-di-tert-butyl-4-hydroxyphenyl) propionic acid e.g. N,N'-bis(3,5-di -tert-butyl-4-hydroxyphenylpropionyl)hexamethylenediamine, N,N'-bis(3,5-di-tert-butyl-4-hydroxyphenylpropionyl) trimethylenediamine, N,N'-bis(3,5-di-tert-butyl-4-hydroxyphenylpropionyl)hydrazine.

1.18. Ascorbic acid (vitamin C)

1.19. Aminic antioxidants, for example N,N'-di-isopropyl-p-phenylenediamine, N,N'-di -sec-butyl-p-phenylenediamine, N,N'-bis(1,4-dimethylpentyl)-p-phenylenediamine, N,N'-bis( 1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p -toluenesulfamoyl) diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n -butylaminophenol, 4-butyrylaminophenol, 4-nonanoylamino-phenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis (phenylamino)propane, (o-tolyl)biguanide, Bis[4-(1',3'-dimethylbutyl) phenyl]amine, tert-octylated N-phenyl-1-naphthylamine, a mixture of mono- and dialkylated tert-butyl/tert -octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octylphenothiazines, N-allylphenothiazin, N,N,N',N'-tetraphenyl-1,4-diaminobut-2-ene, N,N-bis(2,2,6,6-tetramethylpiperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV absorbers and light stabilisers 2.1.2-(2'-Hydroxyphenyl)benzotriazoles, for example 2-(2'-hydroxy-5'-methylphenyl)benzotriazole, 2-(3',5'-di-tert-butyl-2'-hydroxyphenyl) benzotriazole, 2-(5'-tert-butyl-2'-hydroxyphenyl) benzotriazole, 2-(2'-hydroxy-5'-(1,1,3, 3-tetramethylbutyl)phenyl)benzotriazole, 2-(3',5'-di -tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3', 5'-bis-(α,α-dimethylbenzyl)-2'-hydroxyphenyl) benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl) phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$-COO(CH$_2$)$_3$-]$_2$, where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tert -butylbenzoyl) resorcinol, benzoyl resorcinol, 2,4-di -tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p -methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert -butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butyl-benzyl)malonate, 3-n-octyl-7,7,9,9-tetramethyl-1,3,8-triazaspiro[4.5]decan-2,4-dion, bis(1-octyloxy-2,2,6,6-tetramethylpiperidyl)sebacate, bis(1-octyloxy-2,2,6,6-tetramethylpiperidyl)succinate, the condensate of N,N'-bis-(2,2,6,6-tetramethyl-4-piperidyl) hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl) pyrrolidine-2,5-dione, a mixture of 4-hexadecyloxy- and 4-stearyloxy-2,2,6,6-tetramethylpiperidine, a condensation product of N,N'-bis (2,2,6,6-tetramethyl-4-piperidyl)hexamethylenediamine and 4-cyclohexylamino-2,6-dichloro-1,3,5-triazine, a condensation product of 1,2-bis(3-aminopropylamino) ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza -4-oxo-spiro[4,5]decane, a reaction product of 7,7,9,9-tetramethyl-2-cycloundecyl-1-oxa-3,8-diaza-4-oxospiro [4,5]decane and epichlorohydrin, propanedioic acid (4-methoxyphenyl)-methylene-bis(1,2,2,6,6-pentamethyl-4-piperidyl) ester, N,N'-bis-formyl-N,N'-bis(2,2,6,6-tetramethyl-4-piperidyl)-hexamethylenediamine, poly-[methylpropyl-3-oxy-4-(2,2,6,5-tetramethyl-4-piperidyl)]-siloxane, a reaction product of maleic acid-α-olefin copolymer and 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy -5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and ortho- and para-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2- hydroxy-3-butyloxy-propoxy) phenyl]-4,6-bis(2,4-dimethyl)-1,3,5-triazine, 2-[2-hydroxy-4-(2-hydroxy-3-octyloxy -propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy) phenyl]-4,6-bis(2,4-dimethylphenyl)-1,3,5-triazine, 2-(2-hydroxy-4-hexyloxy)phenyl -4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy) phenyl]-1,3,5-triazine, 2-(2-hydroxyphenyl)-4-(4-methoxyphenyl)-6-phenyl-1,3,5 -triazine.

3. Metal deactivators, for example N,N'-diphenyloxamide, N-salicylal-N'-salicyloyl hydrazine, N,N'-bis(salicyloyl) hydrazine, N,N'-bis(3,5-di -tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert -butylphenyl) pentaerythritol diphosphite, bis(2,6-di-tert-butyl-4-methylphenyl) -pentaerythritol diphosphite, diisodecyloxypentaerythritol diphosphite, bis(2,4-di-tert-butyl-6-methylphenyl) pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl)methylphosphite, bis(2,4-di-tert-butyl-6-methylphenyl)ethylphosphite.

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridecyl-nitrone, N-hexadecyl-alpha-pentadecyl-nitrone, N-octadecyl-alpha-heptadecyl -nitrone, N-hexadecyl-alpha-heptadecyl-nitrone, N-ocatadecyl-alpha-pentadecyl -nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers ("ionomers").

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, theology additives, catalysts, flow-control agents, optical brighteners, flameproofing agents, antistatic agents and blowing agents.

14. Benzofuranones and indolinones, for example those disclosed in U.S. Pat. Nos. 4,325,863, 4,338,244, 5,175,312, 5,216,052, 5,252,643, DE-A-4 316 611, DE-A-4 316 622, DE-A-4 316 876, EP-A-0 589 839 or EP-A-0 591 102 or 3-[4-(2-acetoxyethoxy) phenyl]-5,7-di-tert-butyl-benzofuran-2-one, 5,7-di -tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl) benzofuran-2-one, 3-(4acetoxy-3,5-dimethylphenyl)-5,7-di-tert-butyl-benzofuran-2-one, 3-(3,5-dimethyl-4-pivaloyloxyphenyl)-5,7-di-tert -butyl-benzofuran-2-one.

The examples below illustrate the invention in greater detail. Parts and percentages are by weight, both in the examples, in the remainder of the description and in the claims, unless stated otherwise. The calculated analytical data for the polymeric compounds are based on the recurring unit (equivalent to an infinite chain length).

The following abbreviations are used in the examples:
GC: Gas chromatography
HPLC: High-pressure liquid chromatography
GPC: Gel permeation chromatography
THF: Tetrahydrofuran
MALDI: Matrix assisted laser desorption ionization
MS: Mass spectrometry
DSC: Differential scanning calorimetry
$M_n$: Number average molecular weight (unit g/mol)
$M_w$: Weight average molecular weight (unit g/mol)
H-NMR: Proton nuclear magnetic resonance.
1 mmHg corresponds to a pressure of approx. 133 Pa.

A) Preparation examples

A1) 2-Butyn-1,4-diol ditosylate (Compound 1) is prepared as described in Angew. Chem. 104, 1652–1654 (1992).

A2) Preparation of 1,4-bis(4-hydroxy-2,2,6,6-tetramethylpiperidinyl)but-2-yne 833 g (5.3 mol) of 4-hydroxy-2,2,6,6-tetramethylpiperidine and 418 g (1.05 mol) of 2-butyn-1,4-diol ditosylate (Compound 1) in 3.6 l of acetonitrile are introduced under argon into a round-bottom flask fitted with magnetic stirrer and condenser. The mixture is refluxed overnight, poured onto ice and extracted with ethyl acetate. The organic phase is dried and evaporated. The crude product is recrystallized from ethanol, giving 295 g (76%) of the title product of the formula

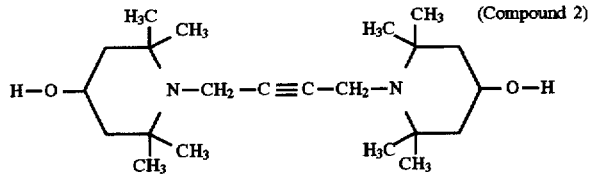 (Compound 2)

as white crystals of melting point 203.4° C.

| Micro analysis | calculated | found |
|---|---|---|
| C | 72.48 | 72.52 |
| H | 11.06 | 11.12 |
| N | 7.68 | 7.75 |

| H-NMR (DMSO) | | |
|---|---|---|
| 1.01 and 1.11 ppm | (24 H, s) | $CH_3$ |
| 1.11–1.19 ppm | (4 H, t) | $CH_2$ (piperidine) |
| 1.60–1.66 ppm | (4 H, m) | $CH_2$ (piperidine) |
| 3.34 ppm | (4 H, s) | $N-CH_2-C\equiv C$ |
| 3.67–3.76 ppm | (2 H, m) | $\diagdown C \diagup O \atop \diagup \phantom{C} \diagdown H$ |
| 4.37–4.39 ppm | (2 H, d) | $-OH$ |

A3) Polycondensation of Compound 2 with dimethyl sebacate

3a) Diol: Diester=1:1

16.91 g (73.4 mmol) of dimethyl sebacate, 26.77 g (73.4 mmol) of Compound 2 and 2 g of dibutyltin oxide are dissolved in 300 ml of xylene in a three-neck round-bottom flask fitted with magnetic stirrer, distillation attachment and argon inlet. The mixture is warmed to 150° C., and a gentle stream of argon is blown through the reaction solution. After 20 hours, the xylene is removed by distillation at 20 mmHg (2666 Pa), and the residue is dried under a high vacuum. The residue is then dissolved in 150 ml of toluene and introduced into acetonitrile, whereupon the polymer precipitates. This operation is repeated. The polyester is dried at 25° C. under a high vacuum, giving 37 g (95%) of white polymer powder.

| | | Microanalysis | calc. | found |
|---|---|---|---|---|
| GPC (THF) | $M_n$ = 6300 | C | 72.41 | 70.20 |
| | $M_w$ = 13400 | H | 10.25 | 10.13 |
| | | N | 5.28 | 4.74 |

3b) Diol: Diester=10:9

20.7 g (90 mmol) of dimethyl sebacate are polycondensed with 36.5 g (0.1 mol) of Compound 2 analogously to Example 3a). 29 g (61%) of polymer are obtained.

| GPC (THF) | $M_n$ = 5400 |
| | $M_w$ = 10600 |

3c) Diol: Diester=10:8

18.4 g (80 mmol) of dimethyl sebacate are polycondensed with 36.5 g (0.1 mol) of Compound 2 analogously to Example 3a). 22 g (52%) of polymer are obtained.

| GPC (THF) | $M_n$ = 3500 |
| | $M_w$ = 6600 |

A4) Polycondensation of Compound 2 with hexamethylene diisocyanate 36.5 g (0.1 mol) of Compound 2 and 16.8 g (0.1 mol) of hexamethylene diisocyanate are dissolved under argon in 200 ml of anhydrous chlorobenzene in a 500 ml round-bottom flask fitted with condenser and magnetic stirrer, and the mixture is refluxed for 8 hours. The solution is poured into acetonitrile, whereupon the polymer precipitates, and is separated off, dissolved in chloroform and re-precipitated in acetonitrile. The white polymer is dried at 50° C. under a high vacuum. Yield 46 g (86%).

| Microanalysis | calculated | found |
|---|---|---|
| C | 67.63 | 66.80 |
| H | 9.84 | 9.98 |
| N | 10.52 | 10.28 |

| GPC (THF) | $M_n$ = 18000 |
| | $M_w$ = 25000 |

A5) Polycondensation of Compound 2 with dimethyl succinate

5a) Diol: Diester=1:1

36.5 g (0.1 mol) of Compound 2, 14.6 g (0.1 mol) of dimethyl succinate and 2.7 g of dibutyltin oxide are dissolved in 400 ml of xylene in a three-neck round-bottom flask fitted with magnetic stirrer, thermometer, argon inlet and distillation attachment. The solution is warmed to 145° C., and a gentle stream of argon is passed through the solution.

When all the methanol has distilled off, the temperature is increased until the solvent distills off.

The residue is dissolved in THF and precipitated in acetonitrile. This operation is repeated, and the polymer is dried at 40° C./0.01 mmHg. Yield 33 g (74%)

| Microanalysis | calculated | found |
|---|---|---|
| C | 69.92 | 67.67 |
| H | 9.48 | 9.51 |
| N | 6.27 | 6.09 |

| GPC (THF) | $M_n$ = 6000 |
| | $M_w$ = 12200 |

5b) Diol: Diester=10:9

36.5 g (0.1 mol) of Compound 2 and 13.2 g (0.09 mol) of dimethyl succinate are polycondensed analogously to Example 5a). 31.5 g (78%) of white polymer powder are obtained.

GPC (THF)

$M_n$=4600

$M_w$=8200

5c) Diol: Diester=10:8

36.5 g (0.1 mol) of Compound 2 are reacted with 11.7 g (0.08 mol) of dimethyl succinate analogously to Example 5a). Yield: 19.2 g (54%).

| GPC (THF) | $M_n$ = 3300 |
| --- | --- |
|  | $M_w$ = 5800 |

A6) Polycondensation of Compound 2 with dimethyl isophthalate 36.5 g (0.1 mol) of Compound 2 are reacted with 19.4 g (0.1 mol) of dimethyl isophthalate analogously to Example 5a). Yield: 35 g (71%)

| Microanalysis | calculated | found |
| --- | --- | --- |
| C | 72.55 | 70.73 |
| H | 8.93 | 8.63 |
| N | 5.64 | 5.12 |
| GPC (THF) | $M_n$ = 5000 | |
|  | $M_w$ = 12500 | |

A7) Polycondensation of Compound 2 with phosgene 36.5 g (0.1 mol) of Compound 2 are taken up in 230 ml of pyridine in a 350 ml sulfonation flask fitted with mechanical stirrer, gas-inlet tube and internal thermometer. Introduction of phosgene at 20° C. causes an exothermic reaction, during the course of which the internal temperature is held at 25°–35° C. The introduction is continued until a viscous suspension is obtained. The flask is subsequently flushed with nitrogen, and the mixture is taken up in 100 ml of methanol and poured into water. The white precipitate is separated off, washed with water, dried, dissolved in dichloromethane and precipitated in ten times the amount of methanol. The white polymer is dried at 30° C. under a high vacuum. Yield: 17.1 g (44%)

| GPC (THF) | $M_n$ = 5400 | |
| --- | --- | --- |
|  | $M_w$ = 11000 | |
| Microanalysis | calculated | found |
| C | 70.73 | 69.82 |
| H | 9.81 | 9.71 |
| N | 7.17 | 7.01 |

A8) Polycondensation of Compound 2 with dibromomethane 112 g of potassium hydroxide are dissolved in 40 ml of water in a 750 ml sulfonation flask fitted with mechanical stirrer, condenser and internal thermometer. A solution of 36.5 g (0.1 mol) of Compound 2 in 200 ml of chlorobenzene is added, followed by 17.4 g (0.1 mol) of dibromomethane. The mixture is warmed to 60° C. with stirring, and 35.5 g (0.11 mol) of tetrabutylammonium bromide are added. After commencement of an exothermic reaction, the internal temperature rises to 77° C. The mixture is stirred at 60° C. for approx. 15 hours, then cooled to 20°–25° C. and diluted with 200 ml of dichloromethane. The mixture is poured into ice-water, the organic phase is separated off, washed with sodium chloride solution and dried using sodium sulfate, and the solvent is removed in a rotary evaporator. The solid residue is extracted with n-hexane for four hours and subsequently dried under a high vacuum. Yield: 23.5 g (62%).

| GPC (THF) | $M_n$ = 935 |
| --- | --- |
|  | $M_w$ = 1320 |

| Microanalysis | calculated | found |
| --- | --- | --- |
| C | 73.36 | 70.54 |
| H | 10.71 | 10.64 |
| N | 7.44 | 7.02 |

A9) Polycondensation of Compound 2 with diphenyldichlorosilane 22.8 g (90 mmol) of diphenyldichlorosilane are dissolved in 250 ml of dioxane in a 750 ml sulfonation flask fitted with magnetic stirrer, dropping funnel, condenser and argon balloon. 36.5 g of Compound 2 are added. 21.2 g (210 mmol) of triethylamine in 50 ml of dioxane are added dropwise to the white suspension at an initial temperature of 20°–25° C., which rises to 39° C. The mixture is warmed to 60° C., stirred for 15 hours and poured into ice-water, the white solid is dried and dissolved in 300 ml of THF, and the solution is introduced dropwise into acetonitrile, whereupon the polymer precipitates. The polymer is dried at 50° C. under a high vacuum. Yield: 36.2 g (74%)

| Analysis | calculated | found |
| --- | --- | --- |
| % C | 74.95 | 74.28 |
| % H | 8.88 | 8.87 |
| % N | 5.14 | 5.00 |
| MALDI-MS | $M_n$ = 3226 | |
|  | $M_w$ = 4942 | |

B) Use examples

Example B1: Light stabilization of polypropylene fibres

In each case, 2.5 g of the novel stabilizer are mixed with 1 g of tris(2,4-di-tert-butylphenyl) phosphite, 1 g of calcium monoethyl 3,5-di-tert-butyl-4-hydroxybenzylphosphonate, 1 g of calcium stearate and 2.5 g of $TiO_2$ (Kronos RN 57) and 1000 g of polypropylene powder (Moplen® FLF 20) in a turbine mixer (melt flow index 12 g/10 min, measured at 230° C./2,16 kg).

The mixtures are extruded at 230° C. to give pellets, which are converted into fibres using a pilot plant (Leonard; Sumirago/VA, Italy) under the following conditions:

Extruder temperature: 230°–240°–245°–260°–255°–255° C.

Stretching ratio: 1:3.5

Stretching temperature: 100° C.

Fibres: 12 den

The fibres produced in this way are exposed against a white background in a Weather-O-Meter® 65WR (Atlas Corp.) with a black panel temperature of 63° C. as described in ASTM D 2565-85. The residual tensile strength of the samples is measured after various exposure times. The measurements are used to calculate the exposure time $T_{50}$ after which only 50% of the original tenacity remains.

For comparative purposes, fibres without the novel stabilizer are produced and tested under otherwise identical conditions. The test results are shown in Table B1.

Table B1: Exposure duration before the initial tensile strength halves

| Stabilizer | Exposure duration |
|---|---|
| none | 220 h |
| from Example A3a | 1620 h |
| from Example A5a | 1460 h |
| from Example A6 | 1200 h |

The fibres stabilized in accordance with the invention have excellent tensile strength retention.

Example B2: Light stabilization of polypropylene tapes

In each case, 1.0 g of the novel stabilizer are mixed with 0.75 g of tris(2,4-di-tert-butylphenyl) phosphite, 0.75 g of calcium monoethyl 3,5-di-tert-butyl-4-hydroxybenzylphosphonate and 1 g of calcium stearate and 1000 g of polypropylene powder (melt flow index 4.0 g/10 min, measured at 230° C./2.16 kg) in a turbine mixer. The mixtures are extruded at 200°–230° C. to give pellets, which are subsequently converted into stretch tapes with a thickness of 50 μm and a width of 2.5 mm using a pilot plant (Leonard; Sumirago/VA, Italy) under the following conditions:

Extruder temperature: 210°–230° C.

Die head temperature: 240°–260° C.

Stretching ratio: 1:6

The tapes produces in this way are exposed against a white background in a Weather-O-Meter® 65WR (Atlas Corp.) with a black panel temperature of 63° C. as described in ASTM D 2565-85. The residual tensile strength of the samples is measured after various exposure times. The measurements are used to calculate the exposure time $T_{50}$ after which only 50% of the original tensile strength remains.

For comparative purposes, fibres without the novel stabilizer are produced and tested under otherwise identical conditions. The test results are shown in Table B2.

Table B2: Exposure duration before the initial tensile strength halves

| Stabilizer | Exposure duration |
|---|---|
| none | 500 h |
| from Example A3a | 1620 h |
| from Example A4 | 1840 h |

The tapes stabilized in accordance with the invention have excellent tensile strength retention.

What is claimed is:

1. A compound of the formula Ia

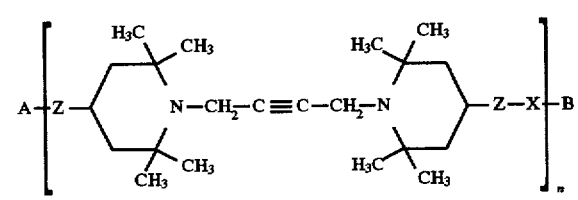

in which n is a number in the range from 4 to 80;

X is —$R^7$—, —CO—, —CO—CO—, —CO—$R^2$—CO—, —CO—NH—$R^5$—NH—CO—, —CO—O—$R^6$—O—CO— or

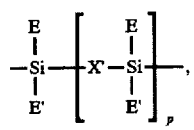

where p is a number in the range from 0 to 6, X' is O or a direct bond, E is $C_1$–$C_{12}$alkyl, phenyl, $C_7$–$C_{12}$phenyl alkyl or $C_5$–$C_{12}$cycloalkyl, and E' is hydrogen or is as defined for E;

Z, when X is $R^7$, is O or $NR^1$;

Z, when X is

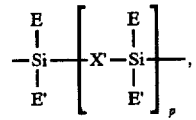

is O; and

Z, in all other cases, is O, NH or $NR^1$;

$R^1$ is $C_1$–$C_8$alkyl, $C_7$–$C_9$phenylalkyl, $C_5$–$C_7$cycloalkyl, $C_2$–$C_8$alkanoyl, benzoyl or $C_1$–$C_4$alkyl-substituted benzoyl;

$R^2$ and $R^7$ are $C_1$–$C_{18}$alkylene; $C_2$–$C_{18}$alkylene which is interrupted by O or S; phenylene; a mixed aromatic/aliphatic radical containing 7 to 12 carbon atoms; naphthylene; or an —$R^4$—D—$R^4$— radical;

$R^4$ is 1,4-cyclohexylene or 1,4-phenylene; and $R^6$ is phenylene, naphthylene or

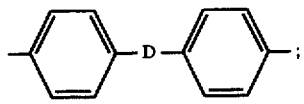

$R^5$, when Z is O, is as defined for $R^2$; and $R^5$, when Z is NH or $NR^1$, is as defined for $R^6$; and D is $C_1$–$C_3$alkylene, —S—, —$SO^2$, —CO—, —O—, —NH— or $NR^1$—;

A is hydrogen or a terminal group of the formula —X—Z';

B is a terminal group of the formula

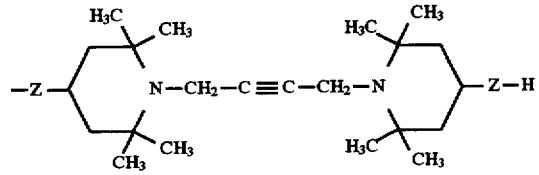

or —Z'; and

Z' is OH, $NH^2$ or $OR^1$.

2. A compound of the formula Ia according to claim 1, in which X is —CO—, —CO—CO—, —CO—$R^2$—CO—,

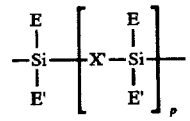

or —CO—NH—$R^5$—NH—CO—, where p is 0 or 1, X' is O or a direct bond, E' is hydrogen, phenyl or methyl, and E is phenyl or methyl;

$R^1$ is $C_1$-$C_8$alkyl, benzyl, $C_2$-$C_8$alkanoyl, benzoyl or cyclohexyl;

$R^2$ and $R^7$ are $C_1$-$C_{18}$alkylene; $C_2$-$C_{18}$alkylene which is interrupted by O or S; phenylene; a mixed aromatic/aliphatic radical containing 7 to 12 carbon atoms; naphthylene; or an —$R^4$—D—$R^4$— radical;

$R^4$ is 1,4-cyclohexylene or 1,4-phenylene;

$R^5$, when Z is O, is $C_3$-$C_{12}$alkylene, phenylene, naphthylene, cyclohexylene, tolylene, ethylene which is interrupted by phenylene, or —$R^4$—$CH_2$—$R^4$—; and D is $C_1$-$C_3$alkylene, —NH—, —$NR^1$, —CO— or —S—.

3. A compound of the formula Ia according to claim 1, in which

Z is O or $NR^1$;

X is —CO—CO—, —CO—$R^2$—CO—,

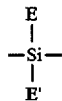

or —CO—NH—$R^5$—NH—CO—;

$R^2$ and $R^7$ are $C_1$-$C_{18}$alkylene; phenylene, $CH_2$—S—$CH_2$, $CH_2$—O—$CH_2$ or

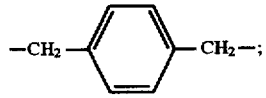

and $R^5$, when Z is O, is $C_3$-$C_{12}$alkylene, phenylene, naphthylene, cyclohexylene, tolylene, ethylene which is interrupted by phenylene, or —$R^4$—$CH_2$—$R^4$—, where $R^4$ is 1,4-cyclohexylene or 1,4-phenylene; and $R^5$, when Z is $NR^1$, is phenylene.

4. A compound of the formula Ia according to claim 3, in which n is an integer in the range from 5 to 50;

Z is an oxygen atom;

$R^2$ and $R^7$ are $C_1$-$C_7$alkylene or phenylene; and $R^5$ is $C_3$-$C_{12}$alkylene, phenylene, naphthylene or cyclohexylene.

5. A composition comprising A) an organic material which is sensitive to oxidative, thermal and/or actinic degradation, and B) a sufficient stabilizing amount of a compound of the formula Ia according to claim 1.

6. A composition according to claim 5, wherein component A is a synthetic organic polymer.

7. A composition according to claim 5, comprising from 0.01 to 10% by weight of the compound of component B, based on the material to be stabilized.

8. A composition according to claim 5, wherein the additional component C is selected from the group consisting of further stabilizers, fillers, reinforcing agents, pigments, dyes, plasticizers, solvents, lubricants, flow-control agents, fluorescent brighteners, nucleating agents, antistatic agents and fire-retarding agents.

9. A process for stabilizing organic material against thermal, oxidative and/or actinic degradation, which comprises adding a compound of the formula Ia according to claim 1 to this material.

10. A compound produced by polycondensation or polyaddition of a compound of the formula II

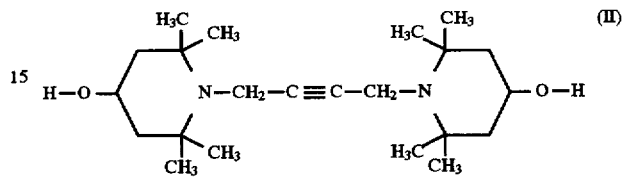

with a bifunctional reaction partner selected from dicarboxylic acids, dichlorides and diesters of dicarboxylic acids of the formula G—CO—$R^2$—CO—G or G—CO—CO—G, in which G is hydrogen, Cl or $C_1$-$C_4$alkoxy; or an anhydride of the formula

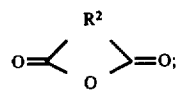

diisocyanates of the formula OCN—$R^5$—NCO; dihalogen compounds of the formula Hal—$R^7$—Hal, in which Hal is in each case a halogen atom; phosgene; $C_1$-$C_4$alkyl carbonic acid diesters; or bischloroformates of the Cl—CO—O—$R^6$—O—CO—Cl type, in which $R^2$, $R^5$ and $R^7$ are $C_1$-$C_{18}$alkylene; $C_2$-$C_{18}$alkylene which is interrupted by O or S; phenylene; a mixed aromatic/aliphatic radical containing 7 to 12 carbon atoms; naphthalene; or an —$R^4$—D—$R^4$— radical;

$R^4$ is 1,4-cyclohexylene or 1,4-phenylene;

$R^6$ is phenylene, naphthalene or

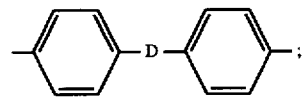

and

D is $C_1$-$C_3$alkylene, —S—, —SO—, —$SO_2$—, —CO—, —O—, —NH— or —$NR^1$.

* * * * *